US012653409B2

(12) United States Patent
Li et al.

(10) Patent No.: US 12,653,409 B2
(45) Date of Patent: Jun. 16, 2026

(54) HEART RATE DETECTION MODULE AND ELECTRONIC DEVICE

(71) Applicant: HUAWEI TECHNOLOGIES CO., LTD., Guangdong (CN)

(72) Inventors: Hangfei Li, Guangdong (CN); Xiaosong Wei, Guangdong (CN); Wenqiang Xia, Guangdong (CN); Hao Zhang, Guangdong (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 41 days.

(21) Appl. No.: 18/715,193

(22) PCT Filed: Nov. 2, 2022

(86) PCT No.: PCT/CN2022/129300
§ 371 (c)(1),
(2) Date: May 31, 2024

(87) PCT Pub. No.: WO2023/098379
PCT Pub. Date: Jun. 8, 2023

(65) Prior Publication Data
US 2025/0025059 A1 Jan. 23, 2025

(30) Foreign Application Priority Data
Dec. 3, 2021 (CN) .......................... 202111471081.X

(51) Int. Cl.
A61B 5/024 (2006.01)
A61B 5/00 (2006.01)

(52) U.S. Cl.
CPC .......... *A61B 5/02427* (2013.01); *A61B 5/681* (2013.01); *A61B 2562/185* (2013.01)

(58) Field of Classification Search
CPC ..... G02B 5/003; A61B 2090/309; A61B 5/24; A61B 5/02438; A61B 5/681;
(Continued)

(56) References Cited

U.S. PATENT DOCUMENTS

| 2004/0222384 | A1* | 11/2004 | Lee | .................... | G01N 21/6452 |
| | | | | | 250/458.1 |
| 2010/0165303 | A1* | 7/2010 | Murata | .................. | G03B 21/10 |
| | | | | | 359/450 |

(Continued)

FOREIGN PATENT DOCUMENTS

| CN | 110179440 A | 8/2019 |
| CN | 209847168 U | 12/2019 |

(Continued)

*Primary Examiner* — Gerald Johnson
(74) *Attorney, Agent, or Firm* — Conley Rose, P.C.

(57) ABSTRACT

A heart detection module includes a light emitting component, a light receiving component, and a Fresnel film, where the light emitting component and the light receiving component are disposed in an optical isolation manner, the Fresnel film is located on a same side of the light emitting component and the light receiving component, and a light outlet surface of the light emitting component faces the Fresnel film. The Fresnel film has a light absorption medium, and in a direction perpendicular to the Fresnel film, the light absorption medium is located between the light emitting component and the light receiving component.

20 Claims, 12 Drawing Sheets

(58) Field of Classification Search
CPC .............. A61B 1/0684; A61B 5/02416; A61B
5/02427; A61B 2562/185
See application file for complete search history.

(56) References Cited

U.S. PATENT DOCUMENTS

| | | | | |
|---|---|---|---|---|
| 2016/0033769 A1* | 2/2016 | Kang | ....................... | G02B 3/08 |
| | | | | 359/13 |
| 2017/0164848 A1* | 6/2017 | Nadeau | .............. | A61B 5/14552 |
| 2019/0090766 A1* | 3/2019 | Block | ................... | H01L 25/167 |
| 2021/0161444 A1 | 6/2021 | Shao et al. | | |

FOREIGN PATENT DOCUMENTS

| | | | |
|---|---|---|---|
| CN | 111936892 A | 11/2020 |
| CN | 113437181 A | 9/2021 |
| JP | 2018101098 A | 6/2018 |
| JP | 2019101412 A | 6/2019 |
| WO | 2016066312 A1 | 5/2016 |

* cited by examiner

HEART RATE DETECTION MODULE AND ELECTRONIC DEVICE

This application is a U.S. National Stage of International Patent Application No. PCT/CN2022/129300 filed on Nov. 2, 2022, which claims priority to Chinese Patent Application No. 202111471081.X filed on Dec. 3, 2021, both of which are hereby incorporated by reference in their entireties.

TECHNICAL FIELD

Embodiments of this application relate to the field of heart rate detection device technologies, and in particular, to a heart rate detection module and an electronic device.

BACKGROUND

Photoplethysmogram (Photoplethysmogram, PPG for short), also referred to as photoelectric plethysmography, is a method for detecting changes in a blood volume caused by beating of heart under a skin tissue of a human body by using a photoelectric technology, and the blood volume changes reflect a pulse wave form and heart rate information. A heart rate detection module (also referred to as a PPG module) detects a pulse and a heart rate of a life body by using a PPG principle.

Generally, the heart rate detection module includes a light emitting component (for example, a light emitting diode) and a photoelectric detector (Photodiode, PD for short) that are disposed at intervals. The light emitting component is configured to emit a detection light beam of a specific wavelength. The PD is configured to receive a light beam that is of the detection light beam and that is reflected or scattered by a human body tissue, and obtain corresponding physiological parameter information such as a heart rate and blood oxygen by analyzing a light beam that carries blood information. In addition, a Fresnel film is disposed on a same side of the light emitting component and the photodiode, the Fresnel film faces a light outlet surface of the light emitting component, and the Fresnel film is configured to converge light beams, to enhance intensity of the detection light beam.

However, the detection light beam emitted by the light emitting component has crosstalk in the Fresnel film, and consequently, a part of the detection light beam enters a photoelectric detector before reaching the human body tissue, affecting detection accuracy of the heart rate detection module.

SUMMARY

Embodiments of this application provide a heart rate detection module and an electronic device, to resolve a problem in a conventional technology that detection accuracy of a heart rate detection module is affected when a light beam emitted by a light emitting component directly passes through a Fresnel film and arrives at a photoelectric detector due to crosstalk in the Fresnel film.

According to a first aspect of embodiments of this application, a heart rate detection module is provided. The heart rate detection module includes a light emitting component, a light receiving component, and a Fresnel film.

The light emitting component and the light receiving component are disposed in an optical isolation manner, the Fresnel film is located on a same side of the light emitting component and the light receiving component, and a light outlet surface of the light emitting component faces the Fresnel film.

The Fresnel film has a light absorption medium, and in a direction perpendicular to the Fresnel film, the light absorption medium is located between the light emitting component and the light receiving component.

In this embodiment of this application, the Fresnel film is disposed on the same side of the light emitting component and the light receiving component, and the Fresnel film is disposed on a side of the light outlet surface of the light emitting component. In this way, light emitted by the light emitting component may be converged through the Fresnel film, that is, the Fresnel film can converge light beams emitted by the light emitting component, so that intensity of a detected light beam can be enhanced. The light absorption medium is disposed in the Fresnel film, and in the direction perpendicular to the Fresnel film, the light absorption medium is located between the light emitting component and the light receiving component. In other words, the light absorption medium disposed in the Fresnel film is located on an optical propagation path of the light emitting component and the light receiving component along the Fresnel film. Therefore, when the light emitted by the light emitting component is propagated in an extension direction of the Fresnel film, that is, some large-angle light formed after the light beams emitted by the light emitting component are converged by the Fresnel film can be absorbed or blocked by the light absorption medium, to cut off, separate, block or isolate an optical path of the light emitted by the light emitting component spreading/transmitting from the Fresnel film to the light receiving component. In other words, a crosstalk phenomenon of a detection light beam emitted by the light emitting component in the Fresnel film can be reduced/weakened, that is, light noise that weakens heart rate measurement due to light leakage in the Fresnel film can be effectively suppressed, and a signal-to-noise ratio of the heart rate detection module is improved. In other words, detection accuracy of the heart rate detection module can be improved.

In addition, compared with a current solution in which a component, for example, a grating is disposed on a side of the Fresnel film, in the heart rate detection module in this embodiment of this application, no other component needs to be additionally disposed, reducing a quantity of components of the heart rate detection module, simplifying an assembly process of the heart rate detection module, improving manufacturing efficiency of the heart rate detection module, and reducing costs. In addition, compared with a current solution in which the Fresnel film is disposed as two parts, a part with a tooth-shaped structure and a part without a tooth-shaped structure, the part with the tooth-shaped structure is aligned with the light outlet surface of the light emitting component, and the part without the tooth-shaped structure is aligned with a light inlet surface of the light receiving component, in this embodiment of this application, the Fresnel film does not need to be accurately assembled between the light emitting component and the light receiving component, reducing assembly precision of the Fresnel film, and improving assembly efficiency of the Fresnel film in this embodiment of this application. In addition, in this embodiment of this application, a light leakage path is optimized, so that a light emitting range of the Fresnel film can be reduced. For example, in this embodiment of this application, light brightness of the Fresnel film on a side of the light inlet surface of the light receiving component can be reduced, improving aesthetics of the Fresnel film.

In an optional design manner, a projection that is of the light absorption medium and that is in a direction parallel to the Fresnel film covers a thickness area of the Fresnel film.

In this way the light absorption medium may cut off, separate, block or isolate an optical propagation path in a thickness direction of the Fresnel film, to avoid a phenomenon that the detection light beam emitted by the light emitting component leaks light in the thickness direction of the Fresnel film (that is, parallel to an extension direction of the Fresnel film), effectively suppressing light noise that weakens heart rate measurement due to light leakage in the Fresnel film, and improving the signal-to-noise ratio of the heart rate measurement module.

In an optional design manner, an accommodating cavity is formed in the Fresnel film, and the light absorption medium is located in the accommodating cavity.

The accommodating cavity is formed in the Fresnel film. In this way, when the light absorption medium is disposed, the light absorption medium may be disposed in the accommodating cavity, so that the light absorption medium can be conveniently connected to the Fresnel film, or the light absorption medium can be conveniently attached to the Fresnel film, to effectively absorb or block light leakage in the Fresnel film. In addition, the disposition of the accommodating cavity may also ensure the integrity of the Fresnel film, facilitating assembly of the Fresnel film.

In an optional design manner, there are a plurality of accommodating cavities, and the plurality of accommodating cavities are disposed at intervals in the Fresnel film.

The plurality of accommodating cavities are disposed at intervals in the Fresnel film. In this way, light leakage of the detection light beam emitted by the light emitting component in the Fresnel film can be absorbed/blocked by light absorption mediums in the plurality of accommodating cavities disposed at intervals, or can be sequentially absorbed/blocked by the light absorption mediums in the plurality of accommodating cavities disposed at intervals, effectively reducing/weakening a light leakage amount in the Fresnel film. In other words, light noise that weakens heart rate measurement due to light leakage in the Fresnel film is efficiently suppressed, and the signal-to-noise ratio of the heart rate detection module is improved. In addition, the plurality of accommodating cavities are disposed at intervals in the Fresnel film, also ensuring structure stability of the Fresnel film. For example, an area between two adjacent accommodating cavities can ensure structure stability of the Fresnel film.

In an optional design manner, a hole is formed on the Fresnel film, and the hole penetrates through two sides of the Fresnel film in the thickness direction; and an inner cavity of the hole is configured as the accommodating cavity.

In this way, the hole is formed on the Fresnel film, and the inner cavity of the hole is configured as the accommodating cavity, so that the accommodating cavity can be conveniently formed on the Fresnel film, forming efficiency of the accommodating cavity can be improved, and a processing process of the accommodating cavity can be simplified. In addition, the inner cavity of the hole is configured as the accommodating cavity. In this way, after the light absorption medium is disposed in the accommodating cavity, the light absorption medium covers the entire thickness direction of the Fresnel film. Therefore, the light leakage amount in the Fresnel film can be effectively reduced/weakened.

In an optional design manner, a plurality of holes are disposed at intervals on the Fresnel film in a first direction, and the first direction is a direction from the light emitting component to the light receiving component.

In this way, light leakage of the detection light beam emitted by the light emitting component in the Fresnel film can be absorbed/blocked layer by layer by the light absorption mediums in the plurality of accommodating cavities disposed at intervals, or can be sequentially absorbed/blocked by the light absorption mediums in the plurality of accommodating cavities disposed at intervals. In other words, light leakage of the detection light beam emitted by the light emitting component in the Fresnel film is partially absorbed when passing through a first layer of light absorption medium, and the light leakage amount is weakened to some extent. When passing through a next layer of light absorption medium, light leakage can be absorbed again. The light leakage mount can be weakened layer by layer, so that the light leakage amount in the Fresnel film can be effectively reduced/weakened. In other words, light noise that weakens heart rate measurement due to light leakage in the Fresnel film is efficiently suppressed, and the signal-to-noise ratio of the heart rate detection module is improved.

In an optional design manner, in the first direction, two adjacent holes have an overlapping area.

Two adjacent holes in the first direction (that is, a direction pointing from the light emitting component to the light receiving component) are disposed to have a specific overlapping area. In this way, in the overlapping area, light absorption mediums in the two adjacent holes can absorb light leakage in the Fresnel film for a plurality of times, so that the light leakage amount in the Fresnel film can be effectively reduced/weakened. In other words, light noise that weakens heart rate measurement due to light leakage in the Fresnel film is efficiently suppressed, and the signal-to-noise ratio of the heart rate detection module is improved.

In an optional design manner, in the first direction, the two adjacent holes partially overlap.

The two adjacent holes can be superimposed through an overlapping part, that is, an extension length of the hole in a direction perpendicular to the first direction can be extended, so that a light absorption medium in the hole can cover or block a larger light leakage area. In other words, the light leakage amount in the Fresnel film can be effectively reduced/weakened. In addition, it can be ensured that a single hole that is in the direction perpendicular to the first direction does not need to cut off or isolate the entire Fresnel film, ensuring integrity and strength of the Fresnel film.

In an optional design manner, the heart rate detection module further includes a light blocking component. The light blocking component is disposed between the light emitting component and the light receiving component, and the light blocking component is configured to support the Fresnel film; and in the direction perpendicular to the Fresnel film, the accommodating cavity and the light blocking component have an overlapping area.

In this disposition manner, the light absorption medium in the accommodating cavity is disposed in the direction perpendicular to the Fresnel film, and the light absorption medium in the accommodating cavity and the light blocking component have an overlapping area, so that a gap between the light absorption medium and the light blocking component can be reduced, effectively avoiding a case in which light is leaked from the gap between the light absorption medium and the light blocking component due to light leakage in the Fresnel film. In other words, light noise that weakens heart rate measurement due to light leakage in the Fresnel film is efficiently suppressed, and the signal-to-noise ratio of the heart rate detection module is improved.

In an optional design manner, the accommodating cavity is a hole, and in the direction parallel to the Fresnel film, at least a part of the hole is in contact with the light blocking component.

In the direction parallel to the Fresnel film, at least a part of the hole is disposed to be in contact with the light blocking component. In this way, a light absorption medium located in the hole can implement seamless contact with the light blocking component in the thickness direction of the Fresnel film, that is, in the direction parallel to the Fresnel film, there is no gap between the light absorption medium in the hole and the light blocking component, avoiding a case in which light is leaked from the gap between the light absorption medium and the light blocking component due to light leakage in the Fresnel film. In addition, because at least a part of the hole is in contact with the light blocking component, the light blocking component can support the hole, ensuring strength of the Fresnel film.

In an optional design manner, there are a plurality of light receiving components, and the plurality of light receiving components are disposed at intervals around the light emitting component; and the plurality of accommodating cavities are disposed at intervals in the Fresnel film around the light emitting component, and in the first direction, the light receiving component and at least a part of the accommodating cavity have an overlapping area.

In other words, when the heart rate detection module has the plurality of light receiving components disposed at intervals around the light emitting component, there may be the plurality of accommodating cavities, and at least a part of the accommodating cavities are located between the light emitting component and the light receiving component. In this way, at least a part of light leakage occurring in the Fresnel film can be absorbed or blocked by the light absorption medium in the accommodating cavity, so that the light leakage amount in the Fresnel film can be reduced/weakened. In other words, light noise that weakens heart rate measurement due to light leakage in the Fresnel film is efficiently suppressed, and the signal-to-noise ratio of the heart rate detection module is improved.

In an optional design manner, the light absorption medium is ink. In this way, when the Fresnel film is manufactured, the light absorption medium can be sprayed by using a spray gun that sprays ink on the Fresnel film, to simplify a processing process of the Fresnel film and reduce a processing device required for the Fresnel film, improving production efficiency of the Fresnel film and reducing production costs.

In an optional design manner, the ink is attached to an inner wall of the accommodating cavity. In this way, only one layer of light absorption medium needs to be attached to the inner wall of the accommodating cavity, and the entire accommodating cavity does not need to be filled with the light absorption medium, so that a material of the light absorption medium can be saved, reducing production costs.

In an optional design manner, a radial section shape of the accommodating cavity includes any one of a circle, a polygon, and an arc.

According to a second aspect of embodiments of this application, an electronic device is provided, including the heart rate detection module provided in any optional design manner of embodiments of the first aspect of this application.

In embodiments of this application, the light absorption medium is disposed in the Fresnel film in the heart rate detection module of the electronic device. When the electronic device detects a heart rate, large-angle light formed due to crosstalk of a detection light beam emitted by the light emitting component on the Fresnel film is absorbed/blocked by the light absorption medium, reducing/weakening crosstalk of the detection light beam emitted by the light emitting component in the Fresnel film, that is, light noise that weakens heart rate measurement due to light leakage in the Fresnel film is efficiently suppressed, and the signal-to-noise ratio of the heart rate detection module is improved. In other words, detection accuracy of the heart rate detection module can be improved, that is, accuracy of heart rate detection performed by the electronic device is improved.

7

Figure 24:
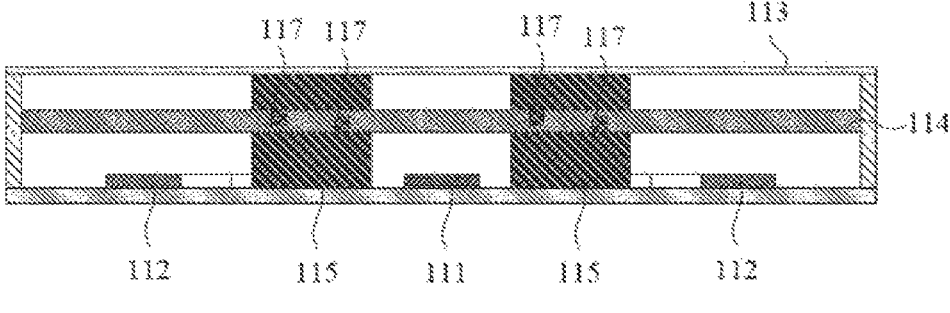

FIG. 24 is yet a further sectional view of a heart rate detection module according to an embodiment of this application.

DESCRIPTIONS OF REFERENCE NUMERALS

10: Electronic device;
100: Device body; 200: Wearing structure; 300: Skin tissue;
110: Heart rate detection module;
111: Light emitting component; 112: Light receiving component; 113: Lens; 114: Fresnel film; 115: Light blocking component; 116: Grating; 117: Light absorption medium; 118: Air gap;
1141: Accommodating cavity; and 1142: Overlapping area.

DESCRIPTION OF EMBODIMENTS

Terms used in embodiments of this application are only used to explain specific embodiments of this application, but are not intended to limit this application.

Figure 1:
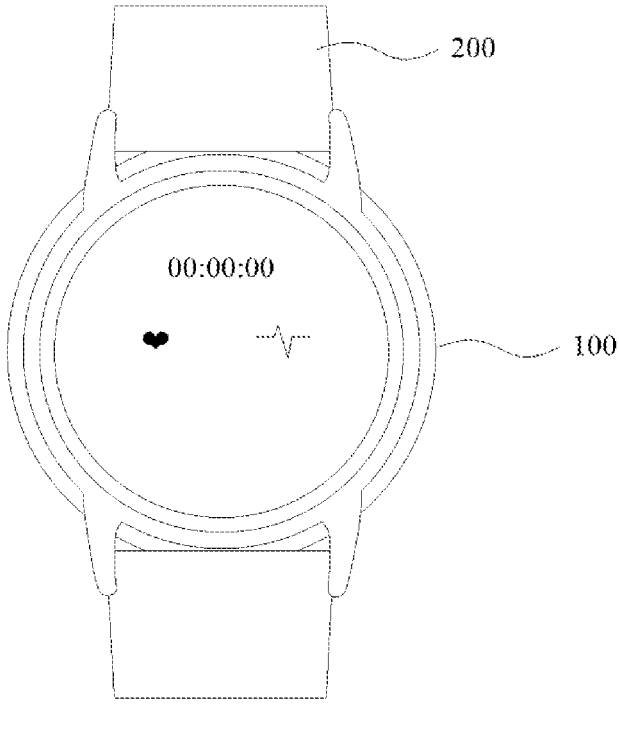
FIG. 1 is a schematic diagram of a structure of an electronic device according to an embodiment of this application.

FIG. 1 is a schematic diagram of a structure of an electronic device according to an embodiment of this application. As shown in FIG. 1, an electronic device 10 provided in this embodiment of this application may be a wearable electronic device 10, for example, an electronic device 10 that can be worn on a human body or a life body, for example, a watch, a band, or a finger ring. A watch is used as a specific example in FIG. 1. It may be understood that a specific type of the electronic device 10 is not limited in FIG. 1. It should be noted that the watch shown in FIG. 1 is shown by using a circular watch face as an example. It should be understood that the watch face of the watch may also be in a rectangular, square, or another polygon shape. The circular watch face in FIG. 1 is merely used as a specific example, and does not specifically limit a shape of the watch face.

It may be understood that, refer to FIG. 1. The electronic device 10 usually includes a device body and a wearing component, and the device body is connected to the wearing component, so that the electronic device 10 is easily worn. A wearing structure 200 may be a wristband shown in FIG. 1. In some possible examples, the wearing structure 200 may also be an annular buckle of a finger ring, an annular band of a neck sleeve, or the like.

Currently, a device body 100 of the wearable electronic device 10 is generally integrated with functions such as making a call and playing music. Because the wearable electronic device 10 is easy to carry and has good skin-fitting, the wearable electronic device 10 may also be used to detect parameters such as a heart rate, a pulse, and blood oxygen of a life body. Specifically, the heart rate, the pulse, and the like of the life body may be detected by using photoplethysmogram.

The photoplethysmogram is also referred to as photoelectric plethysmography, and is a method for detecting, by using a photoelectric technology, a blood volume change caused by a heart beating under a skin tissue 300 of a human. Generally, the blood volume change reflects a pulse wave form and heart rate information. With the development of modern medicine, disease prevention and early discovery are increasingly concerned. To detect a physical abnormality as early as possible, a heart rate detection module (also referred to as a PPG module) 110 is usually used to detect the pulse and the heart rate of the life body by using a PPG principle. In other words, the device body 100 of the electronic device 10 provided in this embodiment of this application includes the heart rate detection module 110.

Figure 2:
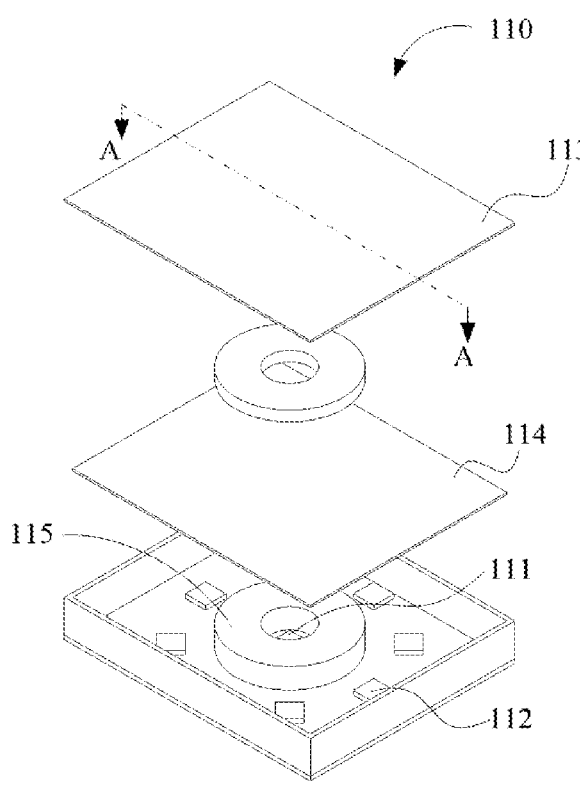
FIG. 2 is a schematic diagram of an exploded structure of a heart rate detection module according to an embodiment of this application.
Figure 3:
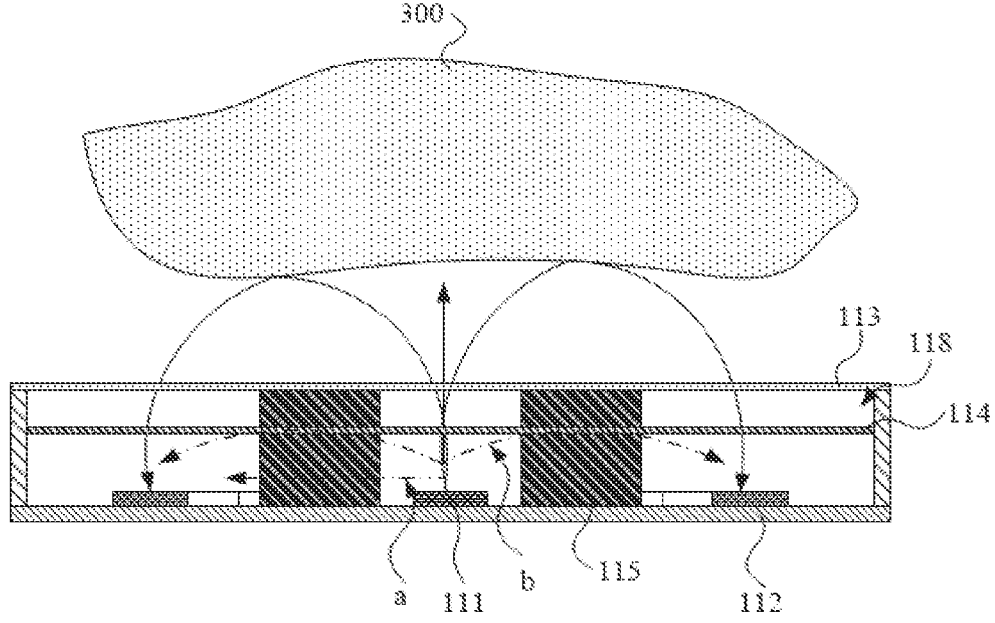
FIG. 3 is a sectional view along an A-A line in FIG. 2.

FIG. 2 is a schematic diagram of an exploded structure of a heart rate detection module according to an embodiment of this application. FIG. 3 is a sectional view along an A-A line in FIG. 2. Refer to FIG. 2 and FIG. 3. A heart rate detection module 110 provided in an embodiment of this application usually includes a light emitting component 111 and a light receiving component 112.

The light emitting component 111 may be a light emitting diode (Light emitting diode, LED for short). In specific disposition, the light emitting component 111 may be disposed on a circuit board (not marked in the figure), and the circuit board may be specifically a printed circuit board (Printed circuit board, PCB), or the circuit board may be an integrated circuit board. A plurality of circuits are printed or integrated on the circuit board, and the LED may be electrically connected to the circuit on the circuit board.

It may be understood that, a power supply battery (not shown in the figure) may be further disposed in an electronic device 10. The power supply battery is connected to the circuit on the circuit board, and is configured to provide electric energy for electronic components (for example, the LED and the light receiving component 112) disposed on the circuit board.

During specific use, refer to FIG. 3. Light emitted by the light emitting component 111 is irradiated on a skin tissue 300 of a life body (for example, a human body). After the light is absorbed, reflected, and scattered by blood, an optical signal carries blood flow information (for example, a heart rate, a pulse, and blood oxygen), and is reflected to the light receiving component 112 by the skin tissue 300. The light receiving component 112 processes the reflected light, to obtain the blood flow information.

The light receiving component 112 may be a photodiode (Photodiode, PD for short). During use, to ensure working performance of the light emitting component 111 and the light receiving component 112, and avoid impact and damage caused by sweat generated by the life body or dust and rain in an external environment to the light emitting component 111, the light receiving component 112, and the component of the circuit board, generally, a lens 113 is disposed on a side of the electronic device 10 facing the life body (that is, when the electronic device 10 is worn, a side closer to a skin of the life body). The lens 113 may be used as a component directly connected to the skin, and is usually a transparent structural component. It may be understood that the lens 113 may be transparent glass, and in some optional examples, the lens 113 may also be transparent resin.

During specific use, a detection light beam emitted by the light emitting component III is radiated to the skin tissue 300 of the life body through the lens 113. After absorption, reflection, and scattering by blood, reflected light flows back to the electronic device 10 after passing through the lens 113, and is received by the light receiving component 112 in the electronic device 10. The light receiving component 112 analyzes a received optical signal (for example, transfers/transmits the received optical signal to a processor for analysis and processing), to obtain the blood flow information.

It may be understood that, the detection light beam emitted by the light emitting component 111 is generally propagated outwards in a divergence manner. To increase an amount of light that is of the detection light beam emitted by the light emitting component 111 and that is irradiated on the skin tissue 300, that is, increase an amount of light of effective detection light beam, an amount of light that can be received by the light receiving component 112 is improved, improving detection accuracy. Refer to FIG. 2 and FIG. 3, generally, the heart rate detection module 110 further includes a Fresnel film 114. The Fresnel film 114 is disposed on a same side of the light emitting component 111 and the light receiving component 112, and a light outlet surface of the light emitting component 111 faces/is opposite to the Fresnel film 114. In other words, the detection light beam emitted by the light emitting component 111 is propagated toward the Fresnel film 114.

It can be learned from the foregoing description that the Fresnel film 114 is located between the light emitting component 111 or the light receiving component 112 and the lens 113. Refer to FIG. 3. The detection light beam emitted by the light emitting component 111 sequentially passes through the Fresnel film 114 and the lens 113, and is radiated to the skin tissue 300 of the life body. A light beam after reflection or scattering of a tissue of the life body and another object sequentially passes through the lens 113 and the Fresnel film 114, and then is received by the light receiving component 112.

It should be noted that, to reduce, lower, or avoid the detection light beam emitted by the light emitting component 111 from directly irradiating the light receiving component 112, reduce a useless optical signal, and improve a signal-to-noise ratio of the heart rate detection module 110, refer to FIG. 2 and FIG. 3. Generally, the light emitting component 111 and the light receiving component 112 are disposed in an optical isolation manner. For example, a light blocking component 115 or an optical blocking wall is disposed between the light emitting component 111 and the light receiving component 112, and the light blocking component 115 may be made of a light absorption material, for example, foam or another black or dark material.

The Fresnel film 114 is usually disposed on the light blocking component 115. In other words, the light blocking component 115 may further support the Fresnel film 114.

The following analyzes, with reference to FIG. 3, an optical propagation path (that is, an optical path) of the detection light beam emitted by the light emitting component 111 in the heart rate detection module 110 according to an embodiment of this application.

It may be understood that light emitted by the light emitting component 111 is generally propagated outward in a divergence manner. In other words, in FIG. 3, one propagation path (a first optical path a in FIG. 3) of the detection light beam emitted by the light emitting component 111 may be directly irradiated by the light emitting component 111 to the light receiving component 112. It may be understood that, a detection light beam of the first optical path a is not reflected or scattered by the skin tissue 300 of the life body. In other words, the detection light beam of the first optical path a does not carry blood flow information (for example, a pulse, a heart rate, and blood oxygen), and is a useless optical signal. As described above, in this embodiment of this application, the light blocking component 115 is disposed between the light emitting component 111 and the light receiving component 112, and the first optical path a is cut off by the light blocking component 115. Therefore, direct illumination of the detection light beam emitted by the light emitting component 111 to the light receiving component 112 can be effectively reduced/weakened, interference of a useless optical signal of the first optical path a to the detection light beam is reduced, and a signal-to-noise ratio of the heart rate detection module 110 is effectively improved.

Refer to FIG. 3. After the detection light beam emitted by the light emitting component 111 is incident to the Fresnel film 114, some large-angle light may be generated in the Fresnel film 114 due to a light converging function of the Fresnel film 114. The large-angle light may be propagated along the Fresnel film 114 (that is, along a second optical path b in FIG. 3) and received by the light receiving component 112. It can be learned that, a detection light beam of the second optical path b that is propagated along the Fresnel film 114 is not reflected or scattered by the skin tissue 300 of the life body, that is, the detection light beam of the second optical path b does not carry blood flow information, and is a useless optical signal.

Figure 4:
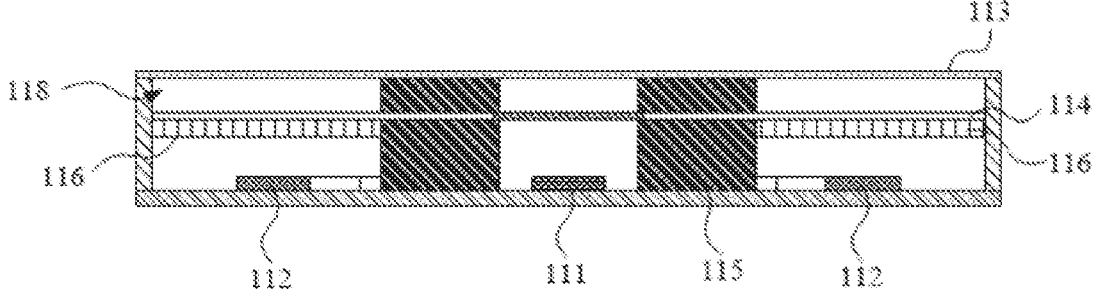
FIG. 4 is a sectional view of a heart rate detection module according to an embodiment of this application.

FIG. 4 is a sectional view of a heart rate detection module according to another embodiment of this application. Refer to FIG. 4. To reduce light leakage in a Fresnel film 114, that is, reduce/weaken interference of a second optical path b to a detection light beam, and improve a signal-to-noise ratio of the heart rate detection module 110, in an embodiment of this application, a heart rate detection module 110 is provided. In the heart rate detection module 110, a tooth-shaped microstructure is disposed on a part that is of the Fresnel film 114 and that is opposite to a light emitting component 111, and a common Fresnel film 114 (that is, no tooth-shaped microstructure is disposed) is disposed on a part that is opposite to the light receiving component 112, in addition, a grating 116 (that is, an optical device formed by a large quantity of equal-width and equal-spaced parallel slits) is disposed on a side that is of the Fresnel film 114 and that faces/is opposite to the light receiving component 112 to filter out light leakage of the Fresnel film 114, so that interference caused by light leakage of the Fresnel film 114 to the detection light beam is reduced, and the signal-to-noise ratio of the heart rate detection module 110 can be effectively improved, that is, measurement accuracy can be improved.

However, it can be learned from the foregoing description that, when the grating 116 is used to filter light leakage of the Fresnel film 114, the grating 116 needs to be used together with the Fresnel film 114, that is, the grating 116 needs to be accurately attached to an area in which no tooth-shaped microstructure is disposed A requirement on precision of a production and assembly process of the heart rate detection module 110 is high, and assembly is difficult. In addition, the grating 116 is added to filter out light leakage of the Fresnel film 114, which also increases a structural complexity of the heart rate detection module 110.

In view of this, this embodiment of this application provides a heart rate detection module 110. A main idea is that a light absorption medium 117 is disposed in the Fresnel film 114, and in a direction perpendicular to the Fresnel film 114, the light absorption medium 117 is disposed between the light emitting component 111 and the receiving component. In other words, the light absorption medium 117 is disposed in the Fresnel film 114, to isolate a light leakage path (that is, the foregoing second optical path) of the Fresnel film 114, so as to reduce, weaken, or eliminate light leakage of the Fresnel film 114, effectively reducing light leakage of a detection beam emitted by the light emitting component 111 when passing through the Fresnel film 114, improving the signal-to-noise ratio of the heart rate detection module 110, and improving detection accuracy of the heart rate detection module 110. In addition, in this embodiment of this application, the light absorption medium 117 is disposed on the light leakage path of the Fresnel film 114 to isolate the light leakage path, so that the Fresnel film 114 does not need to be disposed as different areas. In other words, a processing process of the Fresnel film 114 can be simplified, production efficiency of the Fresnel film 114 can be improved, production efficiency of the heart rate detection module 110 can be improved, and costs can be reduced. In addition, in this embodiment of this application, the light absorption medium 117 is disposed on the light leakage path of the Fresnel film 114 to isolate the light leakage path. In this way, the grating 116 does not need to be attached to a surface of the side that is of the Fresnel film 114 and that faces/is opposite to the light receiving component 112, so that an overall structure of the heart rate detection module 110 can be simplified, an assembly process and a precision requirement of the heart rate detection module 110 can be simplified, and production costs can be reduced.

Figure 5:
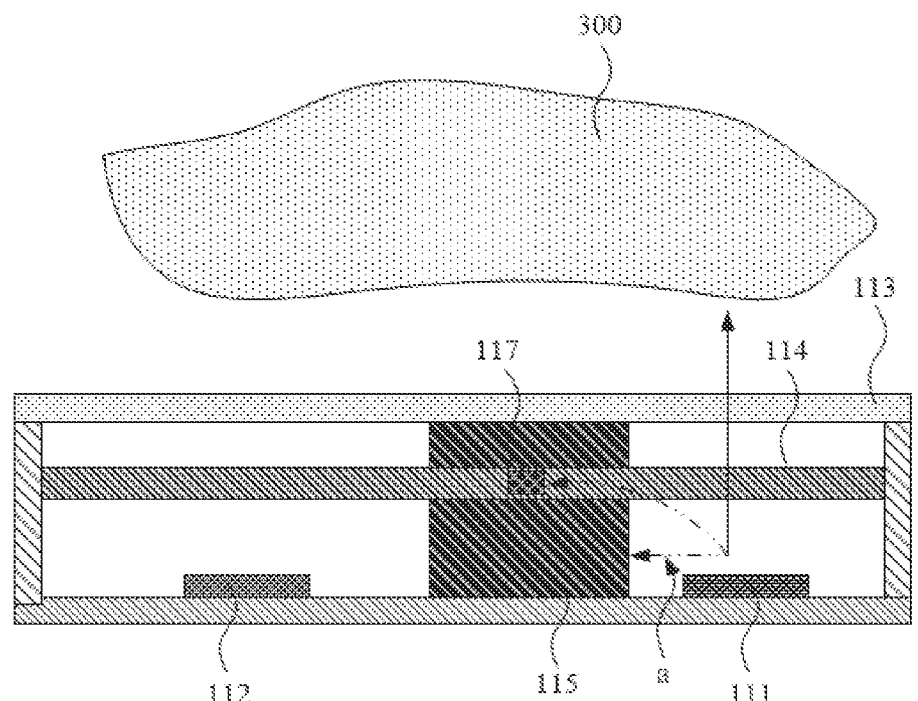
FIG. 5 is another sectional view of a heart rate detection module according to an embodiment of this application.

FIG. 5 is a sectional view of a heart rate detection module according to still another embodiment of this application. Refer to FIG. 5. This embodiment of this application provides a heart rate detection module 110, including a light emitting component 111, a light receiving component 112, and a Fresnel film 114.

Specifically, in this embodiment of this application, the light emitting component 111 may be the foregoing LED light. A detection light beam emitted by an LED may be red light. In some possible examples, the detection light beam emitted by the LED may also be green light. In this embodiment of this application, a specific color of light used as detection light is not limited.

The light emitting component 111 and the light receiving component 112 are disposed in an optical isolation manner. For example, refer to FIG. 3 and FIG. 5. A light blocking component 115 or an optical blocking wall may be disposed between the light emitting component 111 and the light receiving component 112, that is, a sheet-shaped or column-shaped structural component made of an opaque or light absorption material is used, to block the first optical path in FIG. 3.

It may be understood that, because the light emitting component 111 and the light receiving component 112 are disposed on a circuit board, a plurality of cables are usually formed on the circuit board in a manner of printing or deposition. In this way, when the light blocking component 115 or the optical blocking wall is disposed on the circuit board, a small gap may exist between the light blocking component 115 or the optical blocking wall and a surface of the circuit board. Therefore, in this embodiment of this application, the light blocking component 115 or the optical blocking wall may be made of a material having a specific shape variable. For example, the light blocking component 115 or the optical blocking wall may be made of a light absorption material such as foam. In this way, a gap between the light blocking component 115 or the optical blocking wall and the circuit board can be reduced as much as possible, and light leakage occurring in the first optical path can be reduced, so that an optical isolation degree between the light emitting component 111 and the light receiving component 112 can be improved, and a signal-to-noise ratio of the heart rate detection module 110 can be improved.

The Fresnel film 114 is located on a same side of the light emitting component 111 and the light receiving component 112, and a light outlet surface of the light emitting component 111 faces the Fresnel film 114.

In this embodiment of this application, there is a light absorption medium 117 in the Fresnel film 114, and in a direction perpendicular to the Fresnel film 114, the light absorption medium 117 is located between the light emitting component 111 and the light receiving component 112.

The light absorption medium 117 may be made of an opaque material, for example, made of a dark or a black material. In some possible examples, the light absorption medium 117 may be made of a material that is the same as that of the light blocking component 115 or the optical blocking wall.

In this embodiment of this application, the light absorption medium 117 may be formed in the Fresnel film 114 by vapor deposition, deposition, spraying, or the like. For example, when the Fresnel film 114 is manufactured, a groove/dent may be formed on the Fresnel film 114, and then the light absorption medium 117 is formed on an inner wall of the groove/dent in the foregoing manner.

It may be understood that, in some possible embodiments, the light absorption medium 117 may also be filled in the foregoing groove or dent.

With reference to FIG. 3 and FIG. 5, the following analyzes a propagation path of a detection light beam emitted by the light emitting component 111 in this embodiment of this application.

First, light emitted by the light emitting component 111 is propagated outwards in a divergence manner. In a process of propagation along the foregoing first optical path a, the first optical path a is isolated by the light blocking component 115 or the optical blocking wall, so that a detection light beam propagated by the light emitting component 111 along the first path a can be reduced, weakened, or eliminated. Then, after the detection light beam enters the Fresnel film 114, most light rays are radiated to a skin tissue 300 of a life body through a lens 113 under a focusing effect of the Fresnel film 114, and are absorbed, reflected, and scattered by blood. In addition, a small part of detection light forms large-angle light under a reflection effect of the Fresnel film 114, and is propagated along the Fresnel film 114; and when being propagated to the light absorption medium 117, the part of detection light is absorbed and blocked by the light absorption medium 117, and therefore is not received by the light receiving component 112. In other words, the light absorption medium 117 effectively reduces/weakens light leakage of the Fresnel film 114, and reduces impact of light leakage of the Fresnel film 114 on an optical signal received by the light receiving component 112, that is, improves the signal-to-noise ratio of the heart rate detection module 110.

In this embodiment of this application, the Fresnel film 114 is disposed on the same side of the light emitting component 111 and the light receiving component 112, and the Fresnel film 114 is disposed on a side of the light outlet surface of the light emitting component 111. In this way, the light emitted by the light emitting component 111 can be converged through the Fresnel film 114, that is, the Fresnel film 114 can converge a light beam emitted by the light emitting component 111, so that intensity of the detected light beam can be enhanced. The light absorption medium 117 is disposed in the Fresnel film 114, and in the direction perpendicular to the Fresnel film 114, the light absorption medium 117 is located between the light emitting component 111 and the light receiving component 112. In other words, the light absorption medium 117 disposed in the Fresnel film 114 is located on an optical propagation path of the light emitting component 111 and the light receiving component 112 along the Fresnel film 114. Therefore, when the light emitted by the light emitting component 111 is propagated in an extension direction of the Fresnel film 114, some large-angle light formed after the light beam emitted by the light emitting component 111 is converged by the Fresnel film 114 can be absorbed or blocked by the light absorption medium 117, to cut off, separate, block or isolate an optical path of the light emitted by the light emitting component 111 from the Fresnel film 114 to the light receiving component 112. In other words, a crosstalk phenomenon of the detection light beam emitted by the light emitting component 111 in the Fresnel film 114 can be reduced/weakened, that is, light noise that weakens heart rate measurement due to light leakage in the Fresnel film 114 is efficiently suppressed, and the signal-to-noise ratio of the heart rate detection module 110 is improved. In other words, detection accuracy of the heart rate detection module 110 can be improved.

In addition, compared with a case in which a component, for example, a grating 116 is disposed on one side of the Fresnel film 114, in the heart rate detection module 110 in this embodiment of this application, no other component needs to be additionally disposed, reducing a quantity of components of the heart rate detection module 110, simplifying an assembly process of the heart rate detection module 110, improving manufacturing efficiency of the heart rate detection module 110, and reducing costs. In addition, compared with a case in which the Fresnel film 114 is disposed as two parts with a tooth-shaped structure and without a tooth-shaped structure, the part with the tooth-shaped structure is aligned with the light outlet surface of the light emitting component 111, and the part without the tooth-shaped structure is aligned with a light inlet surface of the light receiving component 112. In this embodiment of this application, the Fresnel film 114 does not need to be accurately assembled between the light emitting component 111 and the light receiving component 112, reducing assembly precision of the Fresnel film 114, and improving assembly efficiency of the Fresnel film 114 in this embodiment of this application. In other words, in this embodiment of this application, the light absorption medium 117 is disposed on a light leakage path of the Fresnel film 114 to isolate the light leakage path, so that the Fresnel film 114 does not need to be disposed as different areas. In other words, a processing process of the Fresnel film 114 can be simplified, production efficiency of the Fresnel film 114 can be improved, production efficiency of the heart rate detection module 110 can be improved, and costs can be reduced.

In addition, in this embodiment of this application, the light absorption medium 117 is disposed on the light leakage path of the Fresnel film 114 to isolate the light leakage path. In this way, the grating 116 does not need to be attached to a surface of a side that is of the Fresnel film 114 and that faces/is opposite to the light receiving component 112, so that an overall structure of the heart rate detection module 110 can be simplified, an assembly process and a precision requirement of the heart rate detection module 110 can be simplified, and production costs can be reduced.

In addition, in this embodiment of this application, the light leakage path of the Fresnel film 114 is optimized, so that a light emitting range of the Fresnel film 114 can be reduced. For example, in this embodiment of this application, light of the Fresnel film 114 on a side of the light inlet surface of the light receiving component 112 can be reduced, improving aesthetics of the Fresnel film 114.

Figure 6:
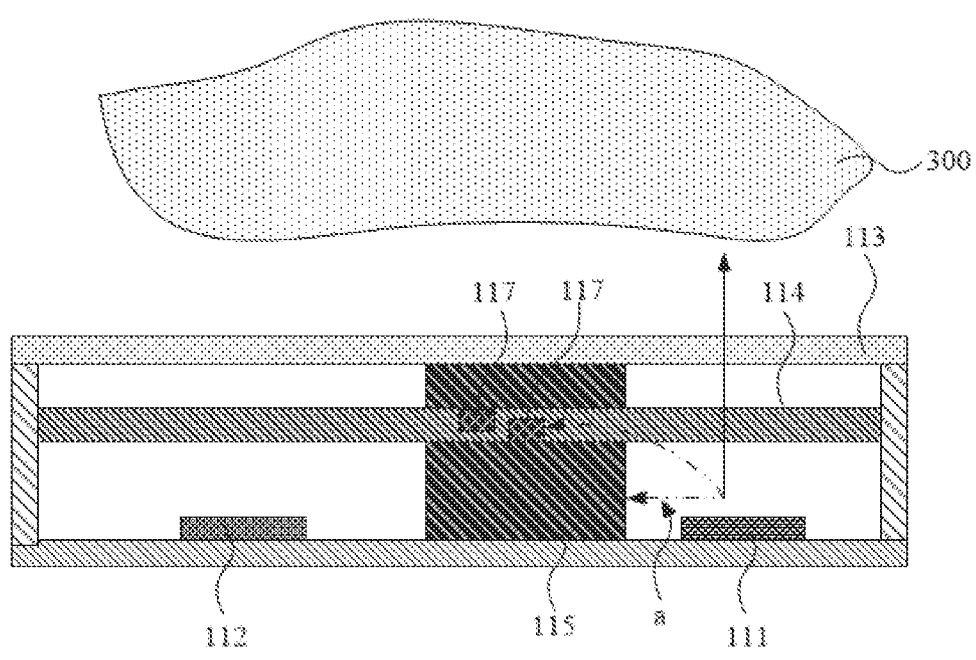
FIG. 6 is still another sectional view of a heart rate detection module according to an embodiment of this application.
Figure 7:
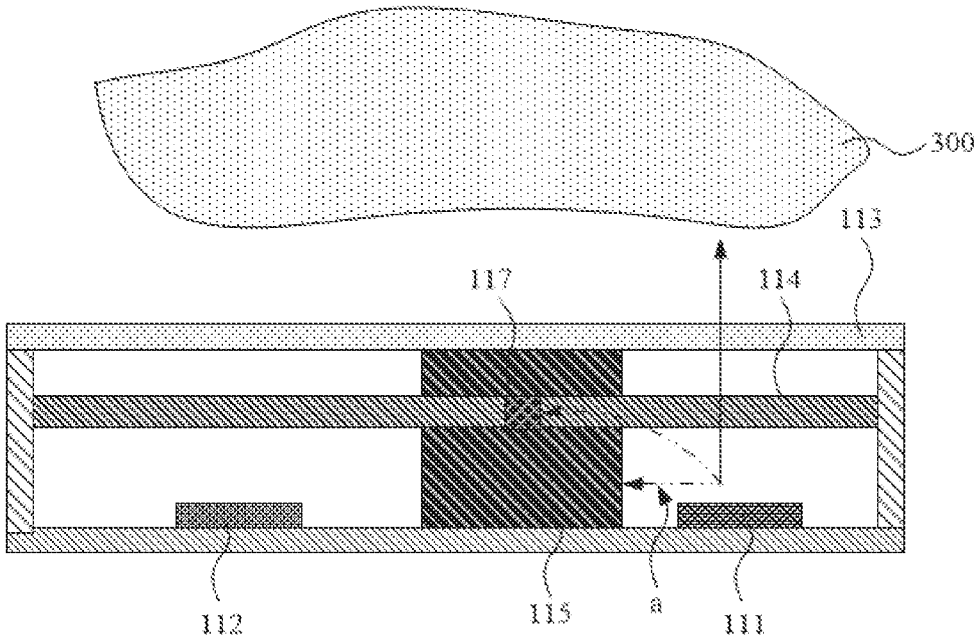
FIG. 7 is yet another sectional view of a heart rate detection module according to an embodiment of this application.

FIG. 6 is another sectional view of a heart rate detection module according to yet another embodiment of this application. FIG. 7 is still another sectional view of a heart rate detection module according to still yet another embodiment of this application. Refer to FIG. 6 and FIG. 7. In this embodiment of this application, a projection that is of a light absorption medium 117 and that is in a direction parallel to the Fresnel film 114 covers a thickness area of a Fresnel film 114.

In other words, in this embodiment of this application, the light absorption medium 117 is disposed on the thickness area of the Fresnel film 114. For example, in some examples, the Fresnel film 114 may be cut off, and the light absorption medium 117 may be disposed on both side walls in a thickness direction of the cut Fresnel film 114. In some other possible examples, an upper surface and a lower surface (for example, as shown in FIG. 7) of the Fresnel film 114 may be separately recessed to form a groove, and the groove is filled with or sprayed with the light absorption medium 117.

In this way, because large-angle light leakage in the Fresnel film 114 usually leaks in the thickness direction of the Fresnel film 114, that is, in this way, the light absorption medium 117 may cut off, separate, block or isolate an optical propagation path in the thickness direction of the Fresnel film 114, avoiding a phenomenon that a detection light beam emitted by a light emitting component 111 leaks light in the thickness direction of the Fresnel film 114 (that is, parallel to an extension direction of the Fresnel film 114), so that light noise that weakens heart rate measurement due to light leakage in the Fresnel film 114 is efficiently suppressed, and a signal-to-noise ratio of the heart rate measurement module is improved.

Figure 8:
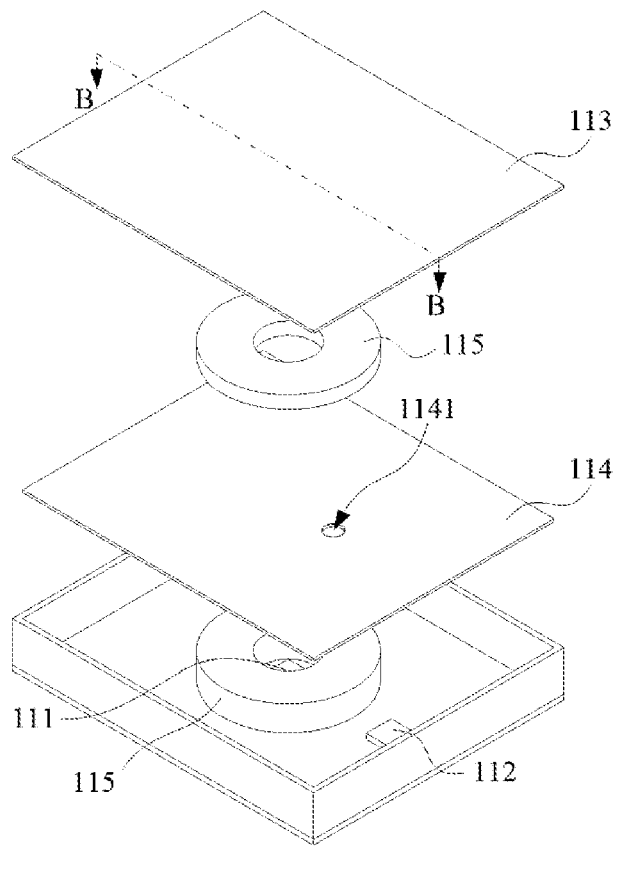
FIG. 8 is a schematic diagram of another exploded structure of a heart rate detection module according to an embodiment of this application.
Figure 9:
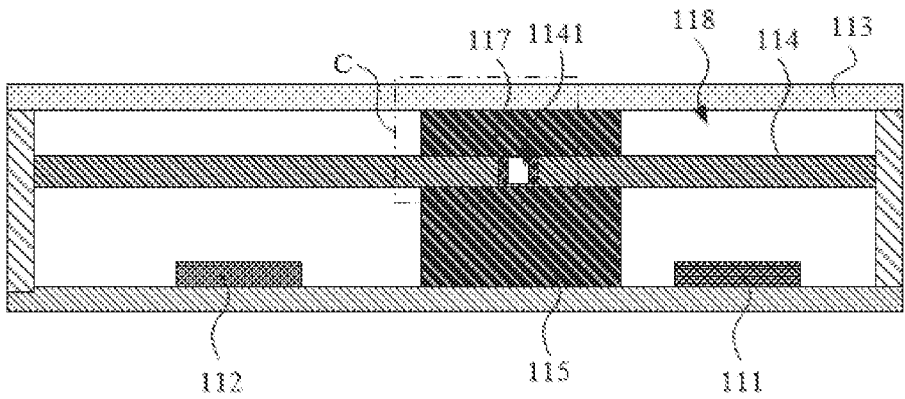
FIG. 9 is a sectional view along a B-B line in FIG. 8.
Figure 10:
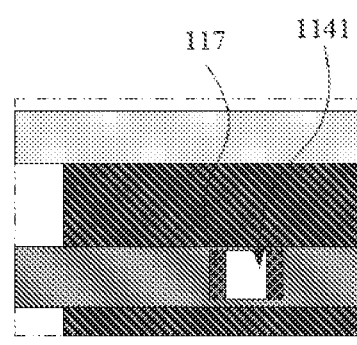
FIG. 10 is a partially enlarged view at a position C in FIG. 9.

FIG. 8 is a schematic diagram of an exploded structure of a heart rate detection module according to another embodiment of this application. FIG. 9 is a sectional view along a B-B line in FIG. 8. FIG. 10 is a partially enlarged view at a position C in FIG. 9. Refer to FIG. 8 to FIG. 10. In an optional example of this embodiment of this application, an accommodating cavity 1141 is formed in a Fresnel film 114, and a light absorption medium 117 is located in the accommodating cavity 1141.

It should be noted that the accommodating cavity 1141 may be formed inside the Fresnel film 114, or may be formed on two surfaces in a thickness direction of the Fresnel film 114. The following separately describes two cases in which the accommodating cavity 1141 is formed inside the Fresnel and on the surface of the Fresnel film.

When the accommodating cavity 1141 is specifically disposed, in a molding process of the Fresnel film 114, for example, in a process of injection molding of the Fresnel film 114, after the Fresnel film 114 is partially molded, the light absorption medium 117 is disposed on a formed part of the Fresnel film 114, and then injection molding is performed on the Fresnel film 114, to form the accommodating cavity 1141 inside the Fresnel film 114. In addition, the light absorption medium 117 is also formed in the Fresnel film 114.

In addition, when the accommodating cavity 1141 is formed on the surface of the Fresnel film 114, the two surfaces in the thickness direction of the formed Fresnel film 114 may be etched to form a groove/dent, and then the light absorption medium 117 is sprayed or filled in the groove or the dent.

The accommodating cavity 1141 is formed in the Fresnel film 114. In this way, when the light absorption medium 117 is disposed, the light absorption medium 117 may be disposed in the accommodating cavity 1141, so that the light absorption medium 117 can be cooperatively connected to the Fresnel film 114, or the light absorption medium 117 can be attached to the Fresnel film 114, to effectively absorb or block light leakage in the Fresnel film 114. In addition, disposition of the accommodating cavity 1141 may also ensure integrity of the Fresnel film 114, facilitating assembly of the Fresnel film 114.

It may be understood that, in this embodiment of this application, after the accommodating cavity 1141 is formed in the Fresnel film 114, and the light absorption medium 117 is disposed in the accommodating cavity 1141, the light absorption medium 117 in the accommodating cavity 1141 can block light leakage of the Fresnel film 114, that is, light leakage occurring along the foregoing second optical path. A blocking effect of the light absorption medium 117 depends on a material and quality of the light absorption medium 117.

Figure 11:
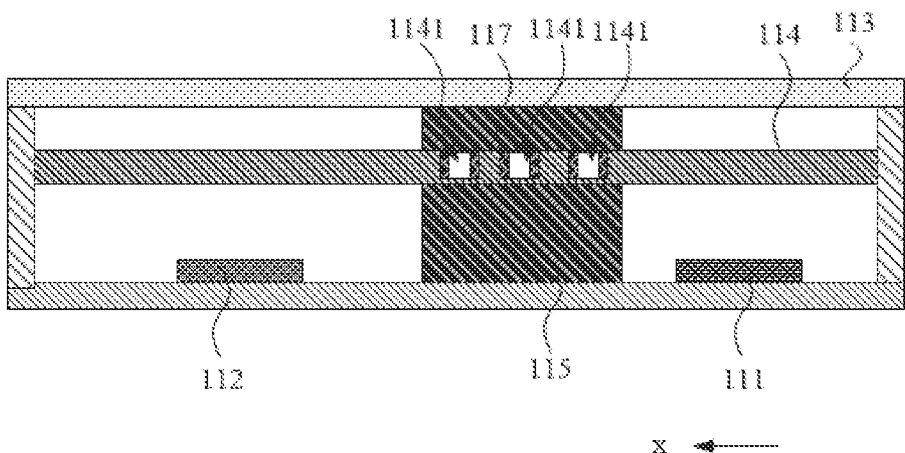
FIG. 11 is still yet another sectional view of a heart rate detection module according to an embodiment of this application.
Figure 12:
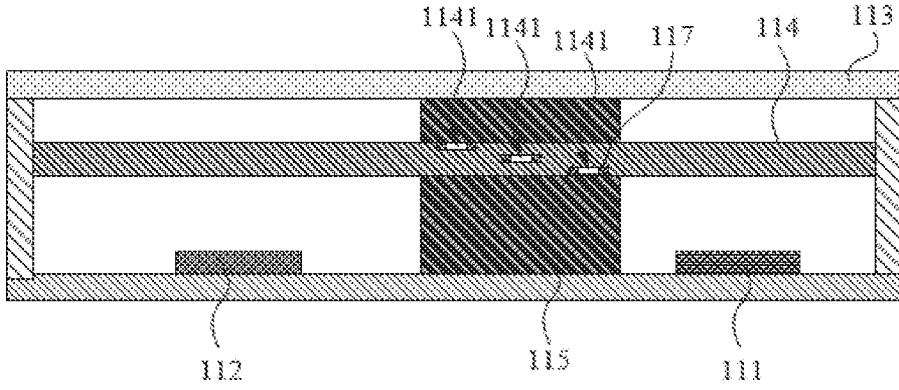
FIG. 12 is a further sectional view of a heart rate detection module according to an embodiment of this application.

FIG. 11 is yet another sectional view of a heart rate detection module according to a further embodiment of this application. FIG. 12 is still yet another sectional view of a heart rate detection module according to still a further embodiment of this application. Refer to FIG. 11 and FIG. 12. In an optional design manner, there are a plurality of accommodating cavities 1141, and the plurality of accommodating cavities 1141 are disposed at intervals in a Fresnel film 114.

It may be understood that in this embodiment of this application, the plurality of accommodating cavities 1141 may be arranged at intervals in an extension direction of the Fresnel film 114, for example, an x direction in FIG. 11. In other words, a plurality of holes are disposed at intervals on the Fresnel film 114 in a first direction, where the first direction is a direction from a light emitting component 111 to a light receiving component 112.

In this way, light leakage of a detection light beam emitted by the light emitting component 111 in the Fresnel film 114 can be absorbed/blocked layer by layer by a light absorption medium 117 in the plurality of accommodating cavities 1141 disposed at intervals, or can be sequentially absorbed/ blocked by the light absorption medium 117 in the plurality of accommodating cavities 1141 disposed at intervals. In other words, light leakage of the detection light beam emitted by the light emitting component 111 in the Fresnel film 114 is partially absorbed by a first layer of the light absorption medium 117, a light leakage amount is weakened to some extent. When passing through a next layer of the light absorption medium 117, light leakage can be absorbed again, and the light leakage amount can be weakened layer by layer, so that the light leakage amount in the Fresnel film 114 can be effectively reduced/weakened. In other words, light noise that weakens heart rate measurement due to light leakage in the Fresnel film 114 is efficiently suppressed, and a signal-to-noise ratio of a heart rate detection module 110 is improved.

In some possible examples, the plurality of accommodating cavities 1141 may alternatively be arranged at intervals in a thickness direction of the Fresnel film 114. In this way, it can be ensured that after the accommodating cavity 1141 is disposed the Fresnel film 114 still has sufficient strength.

The plurality of accommodating cavities 1141 are disposed at intervals in the Fresnel film 114. In this way, light leakage of the detection light beam emitted by the light emitting component 111 in the Fresnel film 114 can be absorbed/blocked by the light absorption medium 117 in the plurality of accommodating cavities 1141 that are disposed at intervals, or can be sequentially absorbed/blocked by the light absorption medium 117 in the plurality of accommodating cavities 1141 that are disposed at intervals, effectively reducing/weakening the light leakage amount in the Fresnel film 114. In other words, light noise that weakens heart rate measurement due to light leakage in the Fresnel film 114 is efficiently suppressed, and the signal-to-noise ratio of the heart rate detection module 110 is improved.

Refer to FIG. 8 to FIG. 10. In an optional design manner of this embodiment of this application, a hole is formed on the Fresnel film 114, and the hole penetrates through two sides of the Fresnel film 114 in the thickness direction; and an inner cavity of the hole is configured as an accommodating cavity 1141.

In other words, in this embodiment of this application, the accommodating cavity 1141 directly penetrates the two surfaces in the thickness direction of the Fresnel film 114. In this way, after the light absorption medium 117 is disposed in the accommodating cavity 1141, the light absorption medium 117 may block in the thickness direction of the Fresnel film 114, blocking/isolating light leakage of the Fresnel film 114.

It may be understood that, in this embodiment of this application, a shape of the hole may be a circular hole, a rectangular hole, a polygonal hole, a strip hole, an arc hole, or the like. A circular hole is used as an example in FIG. 8. It should be understood that the circular hole in FIG. 8 is merely a specific example, and does not limit a specific shape of the hole. When the hole is specifically formed, the hole may be obtained, when the Fresnel film 114 is formed, through integrated molding during injection molding of the Fresnel film 114 by designing a mold. In some possible examples, the hole may also be obtained in a manner of performing secondary processing on the Fresnel film 114 by using a process, for example, hole digging or slotting after the Fresnel film 114 is formed. For example, when the Fresnel film 114 is cut, a cutting shape is designed, to cut the Fresnel film 114 to form the hole.

In this way, the hole is formed on the Fresnel film 114, and an inner cavity of the hole is configured as the accommodating cavity 1141, so that the accommodating cavity 1141 can be conveniently formed on the Fresnel film 114, forming efficiency of the accommodating cavity 1141 can be improved, and a processing process of the accommodating cavity 1141 can be simplified. In addition, the inner cavity of the bole is configured as the accommodating cavity 1141. In this way, after the light absorption medium 117 is disposed in the accommodating cavity 1141, the light absorption medium 117 covers the entire thickness direction of the Fresnel film 114, effectively reducing/weakening a light leakage amount in the Fresnel film 114.

Figure 13:
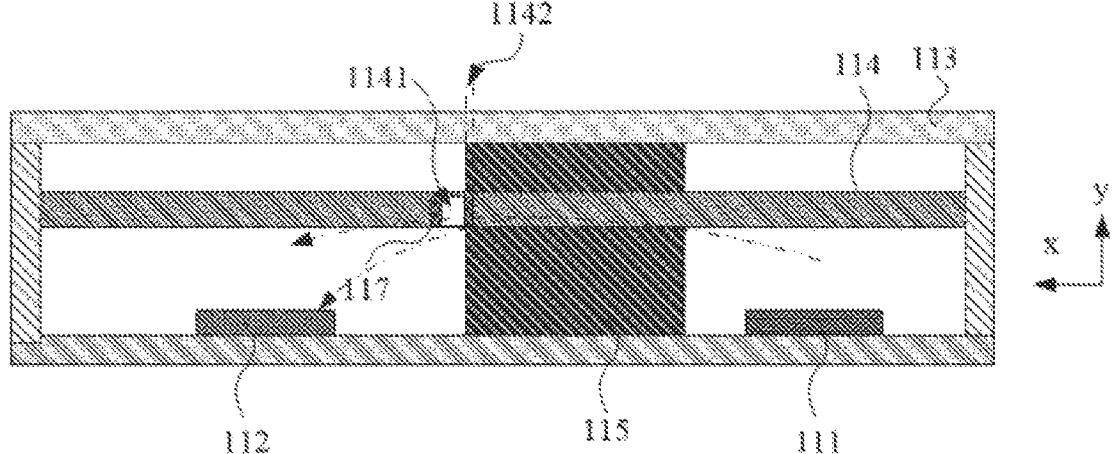
FIG. 13 is still a further sectional view of a heart rate detection module according to an embodiment of this application.
Figure 14:
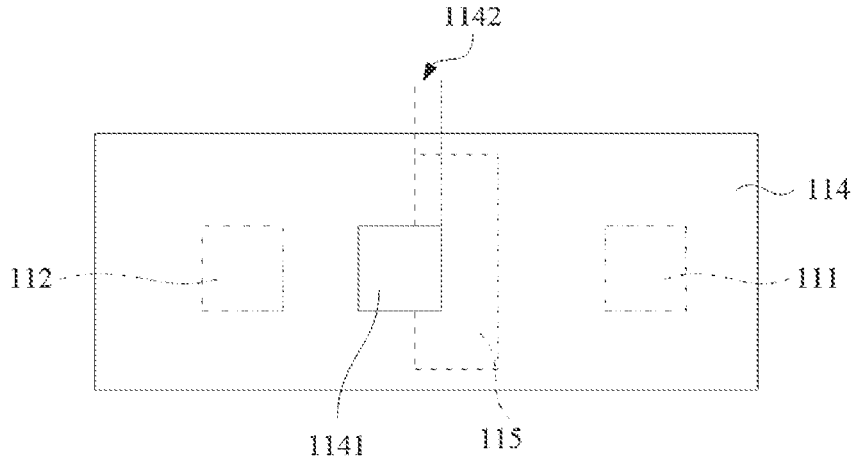
FIG. 14 is a top view of a heart rate detection module according to an embodiment of this application.

FIG. 13 is a further sectional view of a heart rate detection module according to an embodiment of this application. FIG. 14 is a top view of a heart rate detection module according to an embodiment of this application. Refer to FIG. 13 and FIG. 14. In an optional design manner of this embodiment of this application, in a direction perpendicular to a Fresnel film 114, an accommodating cavity 1141 and a light blocking component 115 have an overlapping area 1142.

In other words, in this embodiment of this application, after the Fresnel film 114 is installed on the light blocking component 115, at least a part of the accommodating cavity 1141 located on the Fresnel film 114 is located above the light blocking component 115.

With reference to FIG. 13, the following analyzes a light leakage status in the Fresnel film 114 in the heart rate module according to this embodiment of this application.

Refer to a second optical path b in FIG. 13. When the second optical path b is propagated along the Fresnel film 114, a part of the second optical path b is absorbed or blocked by a light absorption medium 117 in the accommodating cavity 1141. Because the accommodating cavity 1141 and the light blocking component 115 have the overlapping area 1142 in the direction perpendicular to the Fresnel film 114 (that is, a y direction in FIG. 13), a gap between the light absorption medium 117 and the light blocking component 115 in a direction parallel to the Fresnel film (that is, an x direction in FIG. 13) is eliminated. In other words, in this embodiment of this application, the accommodating cavity 1141 is disposed to have the overlapping area 1142 with the light blocking component 115 in the direction perpendicular to the Fresnel film 114. In this way, light leakage that occurs in the gap between the light absorption medium 117 and the light blocking component 115 in the second optical path b in the direction parallel to the Fresnel film (that is, the x direction in FIG. 13) can be eliminated, that is, light noise that weakens heart rate measurement due to light leakage in the Fresnel film 114 is efficiently suppressed, and a signal-to-noise ratio of a heart rate detection module 110 is improved.

Figure 15:
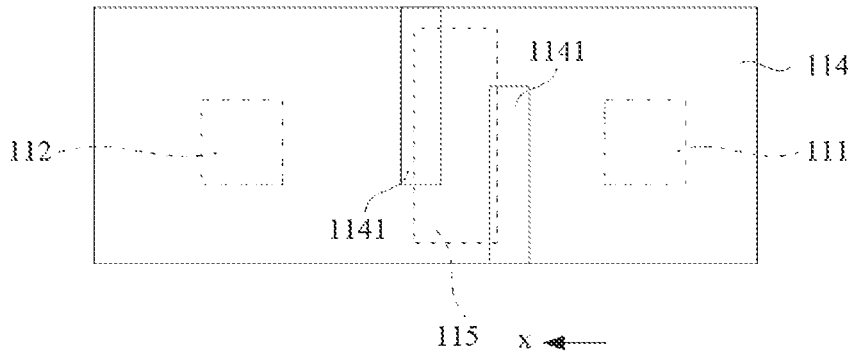
FIG. 15 is another top view of a heart rate detection module according to an embodiment of this application.

FIG. 15 is a top view of a heart rate detection module according to an embodiment of this application. It may be understood that, to facilitate installation of the Fresnel film 114, that is, to directly install the Fresnel film 114 on the foregoing light blocking component 115 or the foregoing optical blocking wall, and improve installation efficiency of the Fresnel film 114, generally, a hole does not directly cut off the Fresnel film 114. In other words, in a first direction, a radial size of the hole is smaller than a size of the Fresnel film 114. In this way, an area that is not covered by the hole exists on the Fresnel film 114, that is, an area that is not covered by a light absorption medium 117 exists. Therefore, refer to FIG. 15. In an optional design manner of this embodiment of this application, in the first direction, two adjacent holes have an overlapping area 1142.

Specifically, the first direction is an extension direction of the Fresnel film 114 or a propagation direction of a second optical path in the Fresnel film 114, for example, an x direction in FIG. 15, that is, a light leakage direction of a detecting light beam in the Fresnel film 114.

The two adjacent holes in the first direction (that is, a direction pointing from a light emitting component 111 to a light receiving component 112) are disposed to have a specific overlapping area 1142. In this way, in the overlapping area 1142, light absorption mediums 117 in the two adjacent holes can absorb light leakage in the Fresnel film 114 for a plurality of times, so that a light leakage amount in the Fresnel film 114 can be effectively reduced/weakened. In other words, light noise that weakens heart rate measurement due to light leakage in the Fresnel film 114 is efficiently suppressed, and a signal-to-noise ratio of a heart rate detection module 110 is improved.

In a specific example, in the first direction, the two adjacent holes partially overlap. In other words, in this embodiment of this application, the two adjacent holes in the first direction are disposed in a staggered manner, and the two holes that are disposed in a staggered manner have an overlapping part. Staggering herein means that there is a staggering relationship between the two holes in a direction perpendicular to the first direction, for example, a y direction in FIG. 14.

The two adjacent holes can be superimposed through the overlapping part, that is, an extension length of the hole in the direction perpendicular to the first direction can be extended, so that the light absorption medium 117 in the hole can cover or block a larger light leakage area. In other words, the light leakage amount in the Fresnel film 114 can be effectively reduced/weakened.

In addition, in this way, it may be ensured that a single hole perpendicular to the first direction does not need to cut off or isolate the entire Fresnel film 114, ensuring integrity and strength of the Fresnel film 114. In addition, installation of the Fresnel film 114 can be facilitated, an installation process of the Fresnel film 114 is simplified, and production efficiency of the heart rate detection module 110 is improved.

Figure 16:
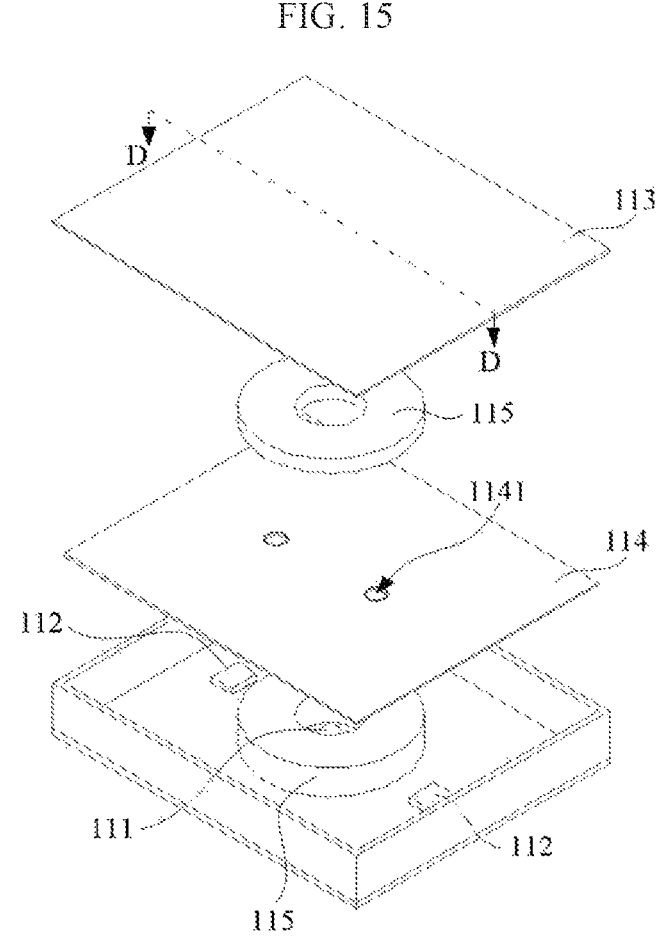
FIG. 16 is a schematic diagram of still another exploded structure of a heart rate detection module according to an embodiment of this application.
Figure 17:
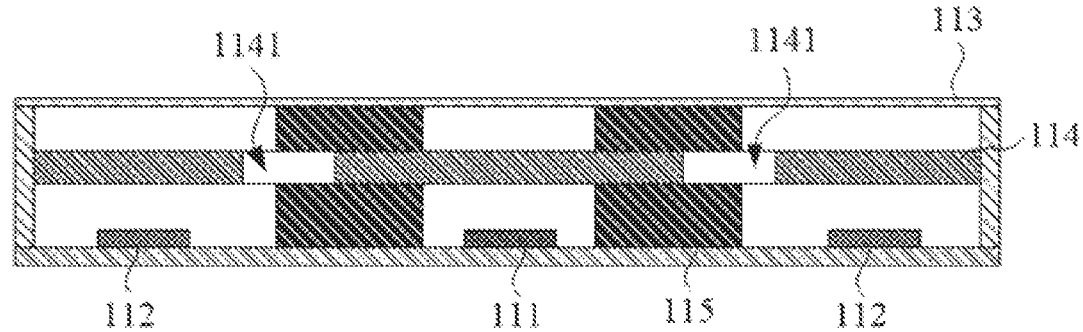
FIG. 17 is a sectional view along a D-D line in FIG. 16.

FIG. 16 is a schematic diagram of another exploded structure of a heart rate detection module according to still another embodiment of this application. FIG. 17 is a sectional view along a D-D line in FIG. 16. Refer to FIG. 16 and FIG. 17. An accommodating cavity 1141 is a hole, and in a direction parallel to a Fresnel film 114, at least a part of the hole is in contact with a light blocking component 115.

It may be understood that, in this embodiment of this application, when the hole penetrates the Fresnel film 114, an edge or an opening of the hole is in contact with the light blocking component 115. Specifically, the edge or the opening of the hole may be in contact with an end that is of the light blocking component 115 and that faces/is opposite to the Fresnel film 114. In this way, after a light absorption medium 117 is disposed in the hole, the light absorption medium 117 can be seamlessly connected to the light blocking component 115, so that light leakage of the Fresnel film 114 can be lowered, weakened, or reduced.

In a direction parallel to the Fresnel film 114, at least a part of the hole is disposed to be in contact with the light blocking component 115. In this way, the light absorption medium 117 located in the hole can implement seamless contact with the light blocking component 115 in a thickness direction of the Fresnel film 114, that is, in a direction parallel to the Fresnel film 114, there is no gap between the light absorption medium 117 and the light blocking component 115 in the hole, so that a case in which light is leaked from a gap between the light absorption medium 117 and the light blocking component 115 due to light leakage in the Fresnel film 114 can be avoided. In addition, because at least a part of the hole is in contact with the light blocking component 115, the light blocking component 115 can support the hole, ensuring strength of the Fresnel film 114.

Figure 18:
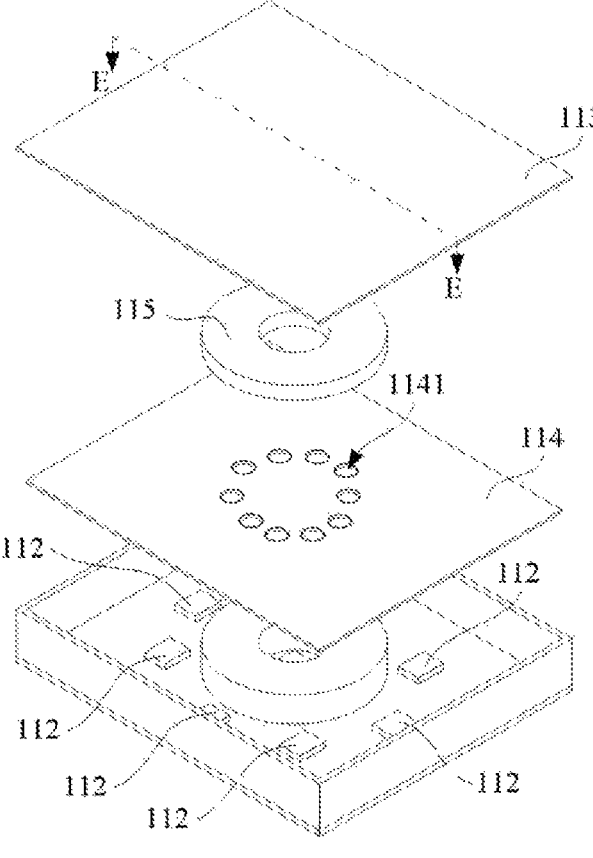
FIG. 18 is a schematic diagram of yet another exploded structure of a heart rate detection module according to an embodiment of this application.
Figure 19:
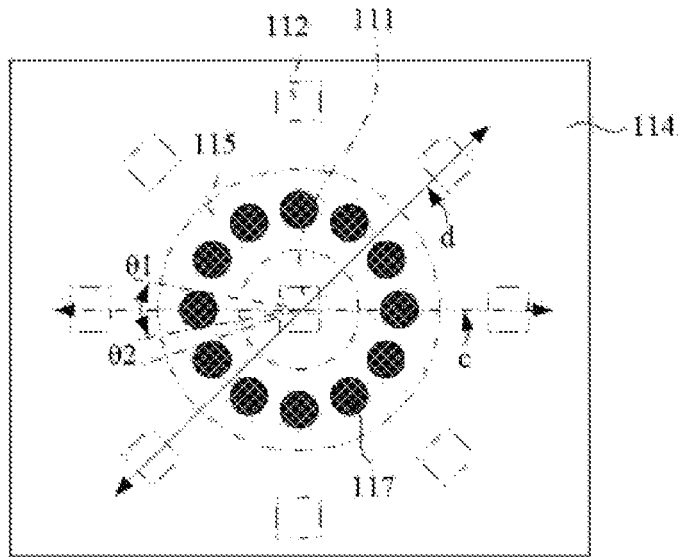
FIG. 19 is a sectional view of an E-E line in FIG. 18.

FIG. 18 is a schematic diagram of still another exploded structure of a heart rate detection module according to an embodiment of this application. FIG. 19 is another top view of a heart rate detection module according to an embodiment of this application. As shown in FIG. 18 and FIG. 19, it should be noted that, to improve accuracy of a heart rate detection module 110, a plurality of light receiving components 112 are usually disposed in the heart rate detection module 110. During specific disposition, to ensure that the plurality of light receiving components 112 can receive even detection optical signals, the plurality of light receiving components 112 are usually disposed at intervals around a light emitting component 111, that is, the plurality of light receiving components 112 may be disposed around the light emitting component 111. In this way, after a detection light beam emitted by the light emitting component 111 is reflected by a skin tissue 300 of a life body, each light receiving component 112 can receive a reflected detection optical signal, and blood flow information is analyzed by combining detection optical signals received by the plurality of light receiving components 112.

It should be noted herein that, in FIG. 19, an example in which a quantity of the light receiving components 112 is 8 is used for illustration. It can be understood that the quantity of the light receiving components 112 may also be another quantity, for example, 6, 9, or more/less. The quantity of the light receiving components 112 shown in the accompanying drawings in this embodiment of this application is merely used as an example for description, and is not specifically limited to the quantity of light receiving components 112.

Refer to FIG. 19. It may be understood that, to avoid light leakage in each direction of a Fresnel film 114 from affecting each light receiving component 112, in this embodiment of this application, a plurality of accommodating cavities 1141 are disposed at intervals around the light emitting component 111 in the Fresnel film 114, and in a first direction, the light receiving component 112 and at least a part of the accommodating cavity 1141 have an overlapping area 1142.

In other words, when the heart rate detection module 110 has the plurality of light receiving components 112 disposed at intervals around the light emitting component 111, there may be the plurality of accommodating cavities 1141, and at least a part of the accommodating cavity 1141 is located between the light emitting component 111 and the light receiving component 112. In this way, at least a part of light leakage occurring in the Fresnel film 114 can be absorbed or blocked by a light absorption medium 117 in the accommodating cavity 1141, so that a light leakage amount in the Fresnel film 114 can be reduced/weakened. In other words, light noise that weakens heart rate measurement due to light leakage in the Fresnel film 114 is efficiently suppressed, and a signal-to-noise ratio of the heart rate detection module 110 is improved.

It is easy to understand that, in this embodiment of this application, when the plurality of light receiving components 112 are disposed at intervals around the light emitting component 111, a light blocking component 115 or an optical blocking wall may be around the light emitting component 111, and be located between the light emitting component 111 and the light receiving component 112. During specific disposition, the light blocking component 115 or the optical blocking wall may be a circular ring, a rectangular ring, or an annular structure of another shape.

It should be noted that, as described above, to facilitate installation of the Fresnel film 114 and improve installation efficiency of the heart rate detection module 110, a hole usually does not cut off the Fresnel film 114, that is, after the hole is formed on the Fresnel, the Fresnel film 114 is still a complete Fresnel film 114. Refer to FIG. 19. A plurality of holes may be disposed at intervals on the Fresnel film 114 around a circumference of the light emitting component 111. In this way, a part between two adjacent holes connects the Fresnel film 114 into a whole, so that integrity and strength of the Fresnel film 114 can be ensured.

It may be understood that, in an actual design, it needs to be ensured that the light absorption medium 117 filled or attached in the hole can absorb or block light leakage occurring in the Fresnel film 114 as much as possible. This requires that a hole diameter of the hole be as large as possible, that is, in FIG. 19, a center of the light emitting component 111 is used as a corner, and a first included angle $\theta 1$ extending between two sides of the hole needs to be as large as possible.

It can be understood that, when the first included angle $\theta 1$ is large to some extent, two adjacent holes may be connected to each other, and consequently, the Fresnel film 114 is divided into two parts, which is unfavorable to installation of the Fresnel film 114. In addition, strength of the Fresnel film 114 is also affected. Therefore, refer to FIG. 20. There is a second included angle $\theta 2$ between the two adjacent holes. It can be learned that a value of the second included angle $\theta 2$ determines strength of the Fresnel film 114.

It should be noted herein that values and value ranges in this embodiment of this application are approximate values. Due to impact of a manufacturing process, an error in a specific range may exist, and a person skilled in the art may consider that the error is negligible.

The following analyzes an optical path in the Fresnel film 114 with reference to FIG. 19. After the detection light beam emitted by the light emitting component 111 enters the Fresnel film 114, some large-angle light may be generated under a light converging function of the Fresnel film 114. The large-angle light is propagated along the Fresnel film 114. When some of the light is propagated to the hole, the light absorption medium 117 disposed in the hole absorbs or blocks the light (for example, a third optical path c in FIG. 19). Another part of the light passes through an interval between two adjacent holes (for example, a fourth optical path d in FIG. 19). It can be learned that, in this embodiment of this application, a reduction degree of light leakage of the Fresnel film 114 is $\theta 1/(\theta 1+\theta 2)$. In some possible determining manners, it may also be $n*\theta 1/360°$, where n is a quantity of holes.

Figure 20:
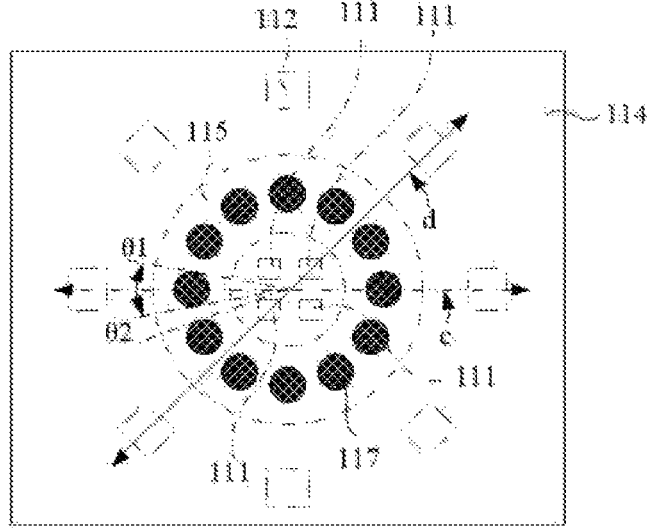
FIG. 20 is still another top view of a heart rate detection module according to an embodiment of this application.

FIG. 20 is still another top view of a heart rate detection module according to an embodiment of this application.

It should be noted that, refer to FIG. 20. In some other optional examples of this embodiment of this application, a heart rate detection module 110 may alternatively include a plurality of light emitting components 111. All the plurality of light emitting components 111 may emit a detection light beam. The plurality of light emitting components 111 have an equivalent center/equivalent axis, and distances from the plurality of light emitting components 111 to the equivalent center/equivalent axis are equal, close, or approximate. In this way, it can be ensured that light emitted by the plurality of light emitting components 111 is evenly distributed and propagated through the equivalent center/equivalent axis. A quantity of the light emitting components 111 shown in FIG. 20 is merely an example for description, and is not a specific limitation on the quantity of the light emitting components 111.

Figure 21:
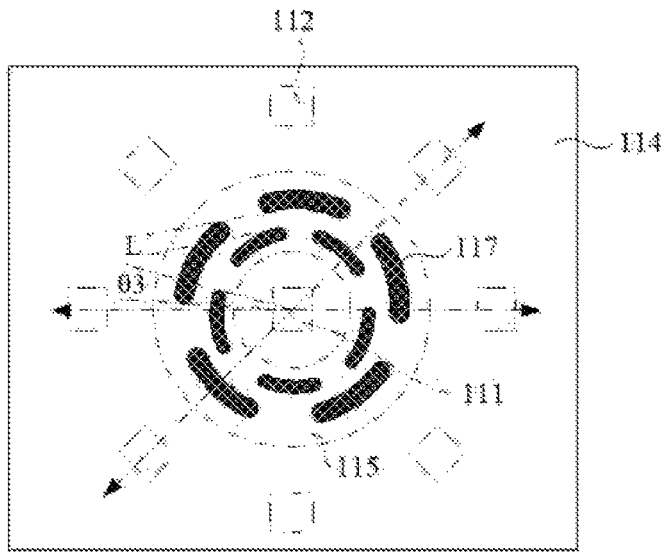
FIG. 21 is yet another top view of a heart rate detection module according to an embodiment of this application.
Figure 22:
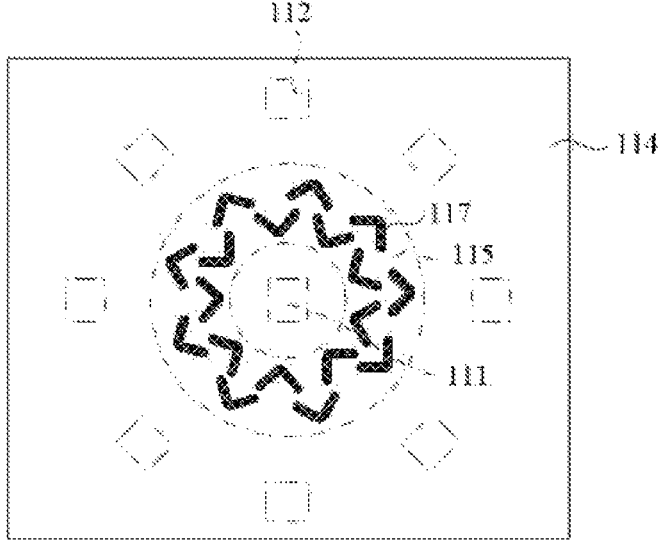
FIG. 22 is still yet another top view of a heart rate detection module according to an embodiment of this application.

FIG. 21 is yet another top view of a heart rate detection module according to an embodiment of this application. FIG. 22 is still yet another top view of a heart rate detection module according to an embodiment of this application. Refer to FIG. 21 and FIG. 22. In this embodiment of this application, a hole may alternatively be a structure of shapes such as an arc hole or a V-shaped hole. Holes are arranged in a plurality of layers/circles in a direction parallel to a Fresnel film 114. It can be learned from FIG. 21 and FIG. 22 that, in a first direction (for example, a direction from a light emitting component 111 to a light receiving component 112), two adjacent holes are disposed in a staggered manner, and the two adjacent holes partially overlap. It can be learned from FIG. 20 that two parameters that affect structural strength and a light leakage status of Fresnel film 114 are an included angle $\theta 3$ of an overlapping area 1142 of the two adjacent holes and a spacing L between the two adjacent holes.

A specific analysis is as follows: If $\theta 3=0$, an inner light absorption arc bole and an outer light absorption arc hole are connected end-to-end, and no overlap or staggering occurs. If $\theta 3>0$, the inner light absorption arc hole and the outer light absorption arc hole have an overlapping area 1142 with an included angle of $\theta 3$. If $\theta 3<0$, the inner light absorption arc hole and the outer light absorption arc hole have a dislocation with an included angle of $\theta$. For example, a quantity of dislocations of inner light absorption arc holes and outer light absorption arc holes is n. In this case, light leakage is reduced to $n*\theta 3/360°$. Therefore, when $\theta 3$ is greater than or equal to 0, the hole may completely isolate light leakage of the Fresnel film 114.

In addition, if L is excessively small, the Fresnel film 114 in an area corresponding to the light emitting component 111 is easily deformed, which is unfavorable for assembly of the Fresnel film 114. In actual application, θ3 and L may be adjusted based on an actual requirement.

It should be noted that, in some possible examples, a plurality of rows, for example, three rows, four rows, or more, of holes may be disposed. For a specific disposition manner, refer to the disposition manners in FIG. 21 and FIG. 22.

With reference to FIG. 21, the following analyzes the light leakage status, that is, an optical path, in the Fresnel film 114. It can be learned that, when there is an overlapping area 1142 between two rows of holes, light leakage in the Fresnel film 114 is completely isolated, and a signal-to-noise ratio of a heart rate detection module 110 is improved.

It should be noted that in this embodiment of this application, the hole is formed on the Fresnel film 114, and an inner cavity of the hole is configured as an accommodating cavity 1141. In this way, after the Fresnel film 114 is processed, only a structural shape of the Fresnel film 114 needs to be cut and modified, for example, the foregoing hole shape (for example, a circular hole, an arc hole, a polygonal hole, or a V-shaped hole) is added to an original cutting shape, and the Fresnel film 114 is cut. In this way, when the Fresnel film 114 is processed, no new processing process needs to be added, so that a processing process of the Fresnel film 114 can be saved, and production and manufacturing efficiency can be improved.

Figure 23:
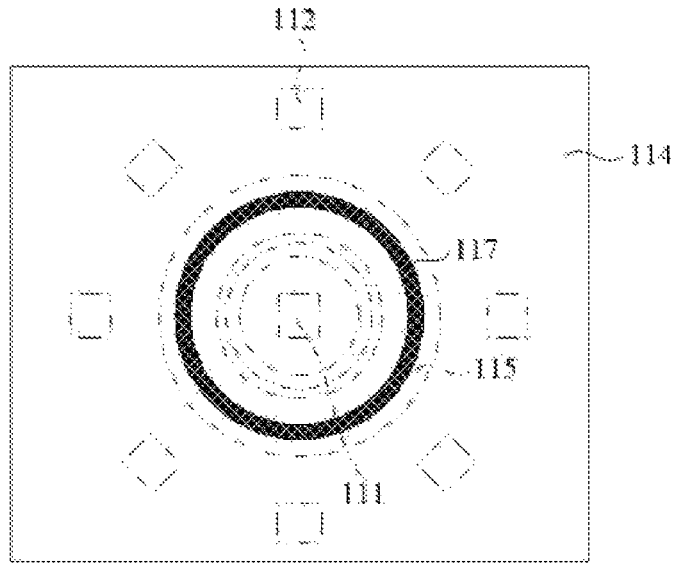
FIG. 23 is a further top view of a heart rate detection module according to an embodiment of this application.

FIG. 23 is a further top view of a heart rate detection module according to an embodiment of this application. FIG. 24 is still a further sectional view of a heart rate detection module according to another embodiment of this application.

Refer to FIG. 23 and FIG. 24. In some other examples, an accommodating cavity 1141 may alternatively be an annular groove around a light emitting component 111. The annular groove may also be two concentric rings arranged in a first direction. Two concentric annular grooves may be separately formed by opening two surfaces of a Fresnel film 114, and the two annular grooves have an overlapping area 1142 in the first direction. In other words, a depth of the annular groove is greater than or equal to half a thickness of the Fresnel film 114.

In some optional examples, to facilitate disposition of a light absorption medium 117, the light absorption medium 117 may be ink. The ink may be light absorption ink. In this way, when the Fresnel film 114 is manufactured, the light absorption medium 117 can be sprayed by using a spray gun that sprays ink on the Fresnel film 114, to simplify a processing process of the Fresnel film 114, and reduce a processing device required by the Fresnel film 114, improving production efficiency of the Fresnel film 114 and reducing production costs.

In addition, the ink is attached to an inner wall of the accommodating cavity 1141. In this way, only one layer of the light absorption medium 117 needs to be attached to the inner wall of the accommodating cavity 1141, and the entire accommodating cavity 1141 does not need to be filled with the light absorption medium 117, so that a material of the light absorption medium 117 can be saved, saving production costs.

During specific production and manufacturing, ink spraying may be performed on an inner wall of a hole in an ink spraying process of the Fresnel film 114, so that the light absorption ink is attached to the inner wall of the hole, and light leakage in the Fresnel film 114 can be isolated. In this way, there is no need to add a processing process, and production costs can be saved.

In addition, it should be noted that, after a detection light beam emitted by the light emitting component 111 passes through the Fresnel film 114 and enters a lens 113, a crosstalk phenomenon exists in the lens 113, that is, light leakage also exists in the lens 113, and a part of light leakage is received by a light receiving component 112. This part of light also does not pass through a skin tissue 300 of a life body, and is useless light. In some optional examples of this embodiment of this application, refer to FIG. 3. A specific gap is reserved between the Fresnel film 114 and the lens 113, to form an air gap 118. Corresponding light is refracted by changing an optical value, reducing optical crosstalk in the lens 113. In the air gap 118, a light blocking component 115 or an optical blocking wall is also disposed in front of the light emitting component 111 and the light receiving component 112.

In descriptions of embodiments of this application, it should be noted that, unless otherwise clearly specified and limited, the terms "installation", "connection to", and "connection" should be understood in a broad sense. For example, the connection may be a fixed connection, may be an indirect connection by using an intermediate medium, or may be an internal connection between two elements or an interaction relationship between two elements. For a person of ordinary skill in the art, specific meanings of the foregoing terms in embodiments of this application may be understood based on a specific situation.

In the specification, claims, and accompanying drawings in embodiments of this application, the terms "first", "second", "third", "fourth", and so on (if available) are intended to distinguish between similar objects but do not necessarily indicate a specific order or sequence.

What is claimed is:

1. A heart rate detection module comprising:
   a light emitting component comprising a light outlet surface;
   a light receiving component, wherein the light emitting component and the light receiving component are optically isolated; and
   a Fresnel film comprising an accommodation cavity that passes through the Fresnel film and a light absorption medium disposed in the accommodation cavity,
   wherein the light emitting component and the light receiving component are disposed on a same side of the Fresnel film, and wherein the Fresnel film faces the light outlet surface, and
   wherein the light absorption medium is disposed between the light emitting component and the light receiving component in a direction perpendicular to the Fresnel film.

2. The heart rate detection module according to claim 1, wherein the light absorption medium has a projection in a direction parallel to the Fresnel film and covers a thickness area of the Fresnel film.

3. The heart rate detection module according to claim 1, wherein the Fresnel film further comprises a plurality of accommodating cavities that are disposed at intervals in the Fresnel film.

4. The heart rate detection module according to claim 3, further comprising a plurality of light receiving components disposed at intervals around the light emitting component, wherein the accommodating cavities are disposed at intervals in the Fresnel film around the light emitting component, wherein the accommodating cavities are disposed at the intervals in a first direction, and wherein the light receiving components and at least a part of the accommodating cavities are overlapping in the first direction.

5. The heart rate detection module according to claim 1, wherein the Fresnel film further comprises a hole that penetrates through two sides of the Fresnel film in a thickness direction, and wherein the hole comprises an inner cavity configured as the accommodating cavity.

6. The heart rate detection module according to claim 5, wherein the Fresnel film further comprises a plurality of holes disposed at intervals on the Fresnel film in a first direction, and wherein the first direction is a direction from the light emitting component to the light receiving component.

7. The heart rate detection module according to claim 6, wherein two adjacent holes in the first direction have an overlapping area.

8. The heart rate detection module according to claim 7, wherein the two adjacent holes are partially overlapping.

9. The heart rate detection module according to claim 1, further comprising a light blocking component disposed between the light emitting component and the light receiving component, wherein the light blocking component is configured to support the Fresnel film, and wherein the accommodating cavity and the light blocking component have an overlapping area in the direction perpendicular to the Fresnel film.

10. The heart rate detection module according to claim 1, wherein the accommodating cavity is a hole, and wherein at least a part of the hole is in contact with the light blocking component in the direction parallel to the Fresnel film.

11. The heart rate detection module according to claim 1, wherein the light absorption medium is ink.

12. The heart rate detection module according to claim 11, wherein the ink is within an inner wall of the accommodating cavity.

13. The heart rate detection module according to claim 1, wherein the accommodating cavity has a radial section shape, and wherein the radial section shape is one of a circle, a polygon, or an arc.

14. An electronic device comprising:
  a heart rate detection module comprising:
    a light emitting component comprising a light outlet surface;
    a light receiving component, wherein the light emitting component and the light receiving component are optically isolated; and a Fresnel film comprising an accommodation cavity that passes through the Fresnel film and a light absorption medium disposed in the accommodation cavity,
    wherein the light emitting component and the light receiving component are disposed on a same side of the Fresnel film, and wherein the Fresnel film faces the light outlet, and
    wherein the light absorption medium is disposed between the light emitting component and the light receiving component in a direction perpendicular to the Fresnel film.

15. The electronic device according to claim 14, wherein the light absorption medium has a projection in a direction parallel to the Fresnel film and covers a thickness area of the Fresnel film.

16. The electronic device according to claim 14, wherein the Fresnel film further comprises a hole that penetrates through two sides of the Fresnel film in a thickness direction, and wherein the hole comprises an inner cavity configured as the accommodating cavity.

17. The electronic device according to claim 14, further comprising a light blocking component disposed between the light emitting component and the light receiving component, and wherein the light blocking component is configured to support the Fresnel film, and wherein the accommodating cavity and the light blocking component have an overlapping area in the direction perpendicular to the Fresnel film.

18. The electronic device according to claim 17, wherein the accommodating cavity is a hole, and wherein at least a part of the hole is in contact with the light blocking component in the direction parallel to the Fresnel film.

19. The electronic device according to claim 14, wherein the Fresnel film further comprises a plurality of holes disposed at intervals on the Fresnel film in a first direction, and wherein the first direction is a direction from the light emitting component to the light receiving component.

20. The electronic device according to claim 19, wherein two adjacent holes in the first direction have an overlapping area.

* * * * *